United States Patent [19]

Lorenz et al.

[11] 4,107,167

[45] Aug. 15, 1978

[54] ALKYL α-[3-(PYRIDYL)-ANILINOMETHYLENE]-ACETOACETATES

[75] Inventors: Roman R. Lorenz; William H. Thielking, both of Schodack, N.Y.

[73] Assignee: Sterling Drug Inc., New York, N.Y.

[21] Appl. No.: 833,484

[22] Filed: Sep. 15, 1977

Related U.S. Application Data

[62] Division of Ser. No. 635,758, Nov. 26, 1975, abandoned, which is a division of Ser. No. 479,627, Jun. 17, 1974, abandoned.

[51] Int. Cl.² ............................................. C07D 213/42
[52] U.S. Cl. .......................... 260/295 R; 260/288 CE; 260/295.5 R; 424/263; 424/266
[58] Field of Search .................... 260/295 R, 295.5 R; 424/263

[56] References Cited

PUBLICATIONS

Chem. Abstracts, 8th Collective Index, p. 5148, −2−[1−(methylamino)ethylidene]−ethyl ester (1966–1975).
Chem. Abstracts, Eck et al., vol. 72, 1972, p. 89719y.

*Primary Examiner*—Natalie Trousof
*Assistant Examiner*—Cary Owens
*Attorney, Agent, or Firm*—Robert K. Bair; B. Woodrow Wyatt

[57] ABSTRACT

Process of reacting 3-PY-aniline (I) with lower-alkyl acetoacetate (II) and tri-(lower-alkyl) orthoformate (III) to produce lower-alkyl α-(3-PY-anilinomethylene)acetoacetate (IV), heating lower-alkyl α-(3-PY-anilinomethylene)acetoacetate (IV), to produce 3-acetyl-1,4-dihydro-4-oxo-7-PY-quinoline (V) which is tautomeric with 3-acetyl-4-hydroxy-7-PY-quinoline (VA), reacting V (or VA) with a lower-alkylating agent to produce 3-acetyl-1-(lower-alkyl)-1,4-dihydro-4-oxo-7-PY-quinoline (VI) and converting VI to 1-(lower-alkyl)-1,4-dihydro-4-oxo-7-PY-3-quinolinecarboxylic acid (VII), where PY is 4(or 3)-pyridyl or 4(or 3)-pyridyl having one or two lower-alkyl substituents. The compounds of formula VII are known antibacterial agents.

2 Claims, No Drawings

ALKYL α-[3-(PYRIDYL)-ANILINOMETHYLENE]ACETOACETATES

This application is a division of copending application Ser. No. 635,738, filed Nov. 26, 1975 and now abandoned, in turn a division of application Ser. No. 479,627, filed June 17, 1974 and now abandoned.

This invention relates to a process for preparing 3-quinolinecarboxylic acids and to compositions used therein.

The invention in a process aspect comprises the four steps of reacting 3-PY-aniline (I) with lower-alkyl acetoacetate (II), and tri-(lower-alkyl) orthoformate (III) to produce lower-alkyl α-(3-PY-anilinomethylene)acetoacetate (IV), heating lower-alkyl α-(3-PY-anilinomethylene)acetoacetate (IV) to produce 3-acetyl-1,4-dihydro-4-oxo-7-PY-quinoline (V) which is tautomeric with 3-acetyl-4-hydroxy-7-PY-quinoline (VA), reacting V (or VA) with a lower-alkylating agent to produce 3-acetyl-1-(lower-alkyl)-1,4-dihydro-4-oxo-7-PY-quinoline (VI) and converting VI to 1-(lower-alkyl)-1,4-dihydro-4-oxo-7-PY-3-quinolinecarboxylic acid (VII), where PY is 4(or 3)-pyridyl or 4(or 3)-pyridyl having one or two lower-alkyl substituents. The final products (VII) are known antibacterial agents. In addition to said combination of the four steps, other process aspects of the invention are each individual step and the consecutive combinations of two or three steps.

The invention in its composition aspect resides in the compounds: lower-alkyl α-(3-PY-anilinomethylene)acetoacetate of the formula IV

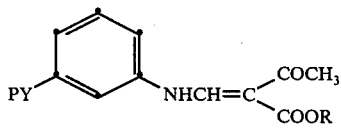    IV where R is lower-alkyl; 3-acetyl-1,4-dihydro-4-oxo-7-PY-quinoline and its tautomeric 3-acetyl-4-hydroxy-7-PY-quinoline of the respective formulas V and VA

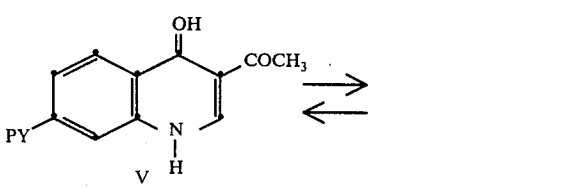

and 3-acetyl-1-(lower-alkyl)-1,4-dihydro-4-oxo-7-PY-quinoline of the formula VI

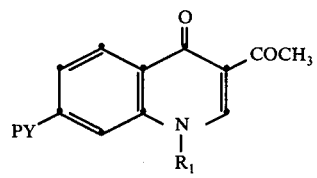    VI where $R_1$ is lower-alkyl and PY in each of the formulas IV, V, VA and VI is defined as hereinabove. Alternatively, the compounds of formulas V and VI can be named 3-acetyl-7-PY-4-(1H)-quinolone and 3-acetyl-1-(lower-alkyl)-7-PY-4-(1H)-quinolone, respectively.

Preferred process and composition embodiments, because of high antibacterial activity of final products and ready availability of intermediates are those where PY is 4-pyridyl, 3-pyridyl, 2-methyl-4-pyridyl and 2,6-dimethyl-4-pyridyl.

The term "lower-alkyl", as used herein, e.g., as represented by R in formula IV or $R_1$ in formula VI, means alkyl radicals having from one to six carbon atoms which can be arranged as straight or branched chains, illustrated by methyl, ethyl, n-propyl, isopropyl, n-butyl, 2-butyl, isobutyl, n-amyl, n-hexyl, and the like.

Illustrative of the PY substituent in I or the PY substituent in formulas IV, V, VA and VI where PY is 4(or 3)-pyridyl having one or two lower-alkyl substituents are the following: 2-methyl-4-pyridyl, 2,6-dimethyl-4-pyridyl, 3-methyl-4-pyridyl, 2-methyl-3-pyridyl, 6-methyl-3-pyridyl (preferably named 2-methyl-5-pyridyl), 2,3-dimethyl-4-pyridyl, 2,5-dimethyl-4-pyridyl, 2-ethyl-4-pyridyl, 2-isopropyl-4-pyridyl, 2-n-butyl-4-pyridyl, 2-n-hexyl-4-pyridyl, 2,6-diethyl-4-pyridyl, 2,6-diethyl-3-pyridyl, 2,6-diisopropyl-4-pyridyl, 2,6-di-n-hexyl-4-pyridyl, and the like. Because of ready availability, ease of preparation and/or high antibacterial activity of the final products, i.e., the 1-(lower-alkyl)-1,4-dihydro-7-[mono(or di)-(lower-alkyl)-4-(or 3)-pyridyl]-4-oxo-3-quinolinecarboxylic acids, preferred embodiments of this group, as noted above, are those where 4(or 3)-pyridyl is substituted by one or two methyl, especially the 2-methyl-4-pyridyl and 2,6-dimethyl-4-pyridyl compounds.

As shown above, 3-acetyl-1,4-dihydro-4-oxo-7-PY-quinoline of formula V is tautomeric with 3-acetyl-4-hydroxy-7-PY-quinoline of formula VA. As with all tautomeric systems, the rate of the transformation V⇌VA and the ratio V/VA are dependent on the thermodynamic environment, including the state of aggregation; so that measurements by any particular techniques do not necessarily have validity except under the conditions of the measurement, thereby, among other consequences, giving rise to problems for any simple designation of the physical embodiments. Thus, measurements of the infrared spectra, in potassium bromide admixture, or in chloroform or mineral oil, indicate existence predominantly as V and the names of the compounds herein therefore are preferably based on structure V, although it is understood that either or both structures are comprehended.

The intermediate 3-PY-anilines (I) are either known or are prepared from known compounds by conventional means.

The molecular structures of the composition aspects (IV, V, VA and VI) of our invention were assigned on the basis of evidence provided by infrared, ultraviolet and nuclear magnetic resonance spectra, by chromatographic mobilities, and, by the correspondence of calculated and found values for the elementary analyses for representative examples.

The manner of making and using the instant invention will now be generally described so as to enable a person skilled in the art of chemistry to make and use the same, as follows:

The preparation of lower-alkyl α-(3-PY-anilinomethylene)acetoacetate (IV) is preferably carried out by heating a mixture of equimolar quantities of 3-PY-aniline (I), tri-(lower-alkyl) orthoformate (III) and lower-alkyl acetoacetate (II) at about 75°–125° C., preferably about 90°–110° C. Although the reaction is conveniently run in the absence of any solvent, it can be run using any solvent inert under the reaction conditions, such as a lower-alkanol, preferably ethanol, acetonitrile, dimethylformamide, benzene, toluene, and the like. Preferably, the reaction is run in the presence of a catalytic amount of an acidic catalyst, e.g., a strong inorganic acid such as hydrochloric acid, sulfuric acid, hydrobromic acid, phosphoric acid, and the like; an organic sulfonic acid such as p-toluenesulfonic acid, benzenesulfonic acid, methanesulfonic acid, ethanesulfonic acid, and the like; a Lewis acid such as zinc chloride, boron trichloride, boron tribromide, aluminum trichloride, and the like. Since the reaction most likely proceeds first by the reaction of the lower-alkyl acetoacetate with the tri-(lower-alkyl) orthoformate to produce lower-alkyl (lower-alkoxy)methyleneacetoacetate which then reacts with 3-PY-aniline to produce IV, the same compound IV optionally can be prepared by reacting 3-PY-aniline with the known lower-alkyl (lower-alkoxy)methyleneacetoacetate. Thus, the process claimed herein comprehends and/or implies the reaction of lower-alkyl acetoacetate with tri-(lower-alkyl) orthoformate to produce lower-alkyl (lower-alkoxy)methyleneacetoacetate and the reaction of the latter with 3-PY-aniline to produce lower-alkyl α-(3-PY-anilinomethylene)acetoacetate (IV).

The reaction of lower-alkyl α-(3-PY-anilinomethylene)acetoacetate (IV) to produce 3-acetyl-1,4-dihydro-4-oxo-7-PY-quinoline (V) is carried out by heating IV in an inert solvent at about 225°–325° C., preferably at about 250°–300° C. Such solvents include mineral oil, diethyl phthalate, dibenzyl ether, the eutectic mixture of diphenyl and diphenyl ether (Dowtherm ®A), and the like.

Alternatively, the above two steps can be run consecutively without isolation of compound IV.

The reaction of 3-acetyl-1,4-dihydro-4-oxo-7-PY-quinoline (V) or its tautomeric 3-acetyl-4-hydroxy-7-PY-quinoline (VA) with a lower-alkylating agent to produce 3-acetyl-1-(lower-alkyl)-1,4-dihydro-4-oxo-7-PY-quinoline (VI) is generally carried out by reacting said compound of formula V or VA with a lower-alkyl ester of a strong inorganic acid or an organic sulfonic acid, said ester having the formula $R_1$-An, where An is an anion of a strong inorganic acid or an organic sulfonic acid, e.g., chloride, bromide, iodide, sulfate, methanesulfonate, benzenesulfonate, and p-toluenesulfonate, and $R_1$ is lower-alkyl. This alkylation is preferably run using a slight excess of the alkylating agent. The chloride, bromide or iodide is preferred because of the ready availability of the requisite lower-alkyl halides; and the reaction is carried out preferably in the presence of an acid-acceptor. The acid-acceptor is a basic substance which preferably forms freely water-soluble by-products easily separable from the product of the reaction, including for example, sodium hydroxide, potassium hydroxide, sodium carbonate, potassium carbonate, sodium alkoxides, potassium alkoxides, sodium amide, diisopropylamine, ethyldiisopropylamine, and the like. The acid-acceptor takes up the hydrogen halide (or HAn) which is split out during the course of the reaction and also takes up the proton from the 1-position of V or from the 4-OH of VA to generate the resulting anion of V or VA. The reaction can be carried out in either the presence of absence of a suitable solvent, but preferably in a solvent such as lower-alkanol, acetone, dioxane, dimethylformamide, dimethyl sulfoxide, hexamethyl phosphoramide, or a mixture of solvent, e.g., a mixture of water and a lower-alkanol. The reaction is generally carried out at a temperature between about room temperature (about 20°–25° C.) and 150° C., preferably heating on a steam bath in a stirred mixture of dimethylformamide and anhydrous potassium carbonate.

The conversion of 3-acetyl-1-(lower-alkyl)-1,4-dihydro-4-oxo-7-PY-quinoline (VI) to 1-(lower-alkyl)-1,4-dihydro-4-oxo-7-PY-3-quinolinecarboxylic acid (VII) is carried out by reacting VI with an agent capable of converting —$COCH_3$ to —COOH. This is conveniently done by reacting VI with chlorine or bromine and an alkali metal hydroxide, preferably sodium or potassium hydroxide, or with the corresponding alkali hypohalite. This conversion of VI to VII also can be carried out by reacting VI with iodine and pyridine followed by reacting the resulting 1-[1-(lower-alkyl)-1,4-dihydro-4-oxo-7-PY-3-quinolinecarbonylmethyl]pyridinium iodide with alkali, e.g., aqueous sodium or potassium hydroxide solution, to convert 3—$COCH_2N^{\oplus}C_5H_5I^{\ominus}$ to 3—COOH; the reaction with the iodine and pyridine is conveniently carried out by heating the reaction mixture on a steam bath and the reaction of the resulting pyridinium iodide compound is conveniently hydrolyzed in refluxing aqueous sodium or potassium hydroxide solution. Alternatively, the conversion of VI to VII is carried out by heating VI with dilute aqueous nitric acid, preferably refluxing 20% nitric acid.

Alternatively, the above-described process can be modified by reacting N-(lower-alkyl)-3-PY-aniline VIII with lower-alkyl acetoacetate (II) and tri-(lower-alkyl) orthoformate (III) to produce lower-alkyl α-[N-(lower-alkyl)-3-PY-anilinomethylene]acetoacetate (IX) and heating IX to produce 3-acetyl-1-(lower-alkyl)-1,4-dihydro-4-oxo-7-PY-quinoline (VI). The ring-closure conversion of IX of produce VI is carried out like the ring-closure conversion of IV to produce V but preferably using polyphosphoric acid at about 175°–235° C.

The best mode contemplated for carrying out the invention is now illustrated as follows:

EXAMPLE 1

Ethyl α-[3-(4-pyridyl)anilinomethylene]acetoacetate

A mixture containing 60 g. of 3-(4-pyridyl)aniline, 46 g. of ethyl acetoacetate, 52 g. of triethyl orthoformate and about 0.1 g. of p-toluenesulfonic acid monohydrate was stirred and heated on a steam bath for 3 hours. The reaction mixture was diluted with about 500 ml. of cyclohexane and stirred while allowing it to cool to room temperature. The mixture was then chilled in an ice bath and the separated solid was collected, washed with n-pentane and recrystallized from isopropyl acetate to produce 52 g. of ethyl α-[3-(4-pyridyl)-anilinomethylene]acetoacetate, m.p. 107°–108° C. A second crop of 20 g. of the same material, m.p. 106°–108° C., was obtained by concentrating and chilling the mother liquor. A sample of this product prepared in another run and recrystallized from cyclohexane was found to melt at 109.5°–110.5° C.

Following the procedure described above in Example 1 but using in place of ethyl acetoacetate and triethyl orthoformate molar equivalent quantities of the appropriate lower-alkyl acetoacetate and tri-(lower-alkyl) orthoformate, there are obtained: methyl α-[3-(4-pyridyl)anilinomethylene]acetoacetate using methyl acetoacetate and trimethyl orthoformate; n-propyl α-[3-(4-pyridyl)anilinomethylene]acetoacetate using n-propyl acetoacetate and tri-n-propyl orthoformate; isopropyl α-[3-(4-pyridyl)anilinomethylene]acetoacetate using isopropyl acetoacetate and isopropyl orthoformate; isobutyl α-[3-(4-pyridyl)anilinomethylene]acetoacetate using isobutyl acetoacetate and triisobutyl orthoformate; and, n-hexyl α-[3-(4-pyridyl)anilinomethylene]acetoacetate using n-hexyl acetoacetate and tri-n-hexyl orthoformate.

EXAMPLE 2

3-Acetyl-1,4-dihydro-4-oxo-7-(4-pyridyl)quinoline

To one liter of boiling Dowtherm® A (eutectic mixture of diphenyl and diphenyl ether) was carefully added with stirring 52 g. of ethyl α-[3-(4-pyridyl)anilinomethylene]acetoacetate and the resulting mixture was boiled for 11 minutes. The reaction mixture was allowed to cool to room temperature (about 25°–30° C.) and allowed to stand overnight. The precipitate was collected, washed with a small amount of benzene and recrystallized from dimethylformamide to produce 14 g. of 3-acetyl-1,4-dihydro-4-oxo-7-(4-pyridyl)quinoline (or 3-acetyl-7-(4-pyridyl)-4(1H)-quinolone), m.p. >300° C. A second crop of 13.6 g. of this product, m.p. >300° C., was obtained after precipitation from the reaction mixture and recrystallization from dimethylformamide.

3-Acetyl-1,4-dihydro-4-oxo7-(4-pyridyl)quinoline also is produced by following the above-described procedure but using in place of ethyl α-[3-(4-pyridyl)anilinomethylene]acetoacetate a molar equivalent quantity each of the following lower-alkyl α-[3-(4-pyridyl)anilinomethylene]acetoacetates: methyl, n-propyl, isopropyl, isobutyl or n-hexyl α-[3-(4-pyridyl)anilinomethylene]acetoacetate.

EXAMPLE 3

3-Acetyl-1-ethyl-1,4-dihydro-4-oxo-7-(4-pyridyl)quinoline

To a mixture containing 22 g. of 3-acetyl-1,4-dihydro-4-oxo-7-(4-pyridyl)quinoline and 200 ml. of dimethylformamide was added 22 g. of anhydrous potassium carbonate and the resulting mixture was stirred and heated on a steam bath for about 15 minutes. To said mixture heated on a steam bath was added dropwise with stirring a solution of 18 g. of ethyl tosylate in 30 ml. of dimethylformamide. The reaction mixture was then stirred over a steam bath for two hours and the solvent distilled off in vacuo. The residue was shaken well with a mixture of water and chloroform. The layers were then separated and the chloroform layer evaporated in vacuo to remove the chloroform. The residue was recrystallized once from dimethylformamide and once from acetonitrile to produce 18.0 g. of 3-acetyl-1-ethyl-1,4-dihydro-4-oxo-7-(4-pyridyl)quinoline (or 3-acetyl-1-ethyl-7-(4-pyridyl)-4(1H)-quinolone), m.p. 231°–233° C.

EXAMPLE 4

1-Ethyl-1,4-dihydro-4-oxo-7-(4-pyridyl)-3-quinolinecarboxylic acid

To a cold (0° C.) solution containing 3 g. of sodium hydroxide in 28 ml. of water was added 1.54 ml. of bromine. To the resulting solution kept at 0° C. was added with stirring 3.0 g. of 3-acetyl-1-ethyl-1,4-dihydro-4-oxo-7-(4-pyridyl)quinoline and the resulting reaction mixture was stirred while allowing it to warm up to room temperature and then to stand at room temperature for several hours. The reaction mixture was then acidified with glacial acetic acid and the resulting precipitate was collected and recrystallized twice from dimethylformamide, using decolorizing charcoal during the second recrystallization, to produce 2 g. of 1-ethyl-1,4-dihydro-4-oxo-7-(4-pyridyl)-3-quinolinecarboxylic acid, m.p. 260°–285° C.; this compound was established to be the same as an authentic sample of 1-ethyl-1,4-dihydro-4-oxo-7-(4-pyridyl)-3-quinolinecarboxylic acid by side-by-side, thin layer chromatographic comparison wherein the chromatographic mobilities and ultraviolet spectra of the two compounds were found to be identical.

The conversion of 3-acetyl-1-ethyl-1,4-dihydro-4-oxo-7-(4-pyridyl)quinoline to 1-ethyl-1,4-dihydro-4-oxo-7-(4-pyridyl)-3-quinolinecarboxylic acid also is carried out alternatively as follows: by warming on a steam bath for 90 minutes a mixture containing 1.46 g. of 3-acetyl-1-ethyl-1,4-dihydro-4-oxo-7-(4-pyridyl)quinoline, 2.4 ml. of pyridine and 0.86 g. of iodine, allowing the reaction mixture to stand overnight at room temperature, removing the excess pyridine in vacuo, drying the residue in vacuo at 130° C., heating the residue under reflux for 1 hour in 35 ml. of 1N potassium hydroxide solution in diethylene glycol which contained 1 ml. of water, diluting the solution with water, acidifying the solution with hydrochloric acid, extracting the mixture with ether, extracting the product from the ether with dilute sodium bicarbonate, decolorizing the resulting aqueous solution with decolorizing charcoal, acidifying the resulting solution and collecting the crystalline 1-ethyl-1,4-dihydro-4-oxo-7-(4-pyridyl)-3-quinolinecarboxylic acid.

In another conversion of the 3-acetyl compound to 1-ethyl-1,4-dihydro-4-oxo-7-(4-pyridyl)-3-quinolinecarboxylic acid, a 1.46 g. portion of said 3-acetyl compound is refluxed for 5 hours with 35 ml. of 20% nitric acid, the reaction mixture is evaporated to dryness in vacuo, the residue is boiled for 15 minutes with acetic acid, the separated 3-carboxylic acid is collected and recrystallized from acetonitrile.

Following the procedures described in Example 1 but using in place of 3-(4-pyridyl)aniline a molar equivalent quantity of the appropriate 3-PY-aniline, the compounds of Examples 5–11 are obtained:

EXAMPLE 5 — Ethyl α-[3-(3-pyridyl)anilinomethylene]-acetoacetate using 3-(3-pyridyl)aniline.

EXAMPLE 6 — Ethyl α-[3-(2-methyl-4-pyridyl)anilinomethylene]acetoacetate using 3-(2-methyl-4-pyridyl)aniline.

EXAMPLE 7 — Ethyl α-[3-(3-methyl-4-pyridyl)anilinomethylene]acetoacetate using 3-(3-methyl-4-pyridyl)aniline.

EXAMPLE 8 — Ethyl α-[3-(2-ethyl-4-pyridyl)anilinomethylene]acetoacetate using 3-(2-ethyl-4-pyridyl)aniline.

EXAMPLE 9 — Ethyl α-[3-(3-ethyl-4-pyridyl)anilinomethylene]acetoacetate using 3-(3-ethyl-4-pyridyl)aniline.

EXAMPLE 10 — Ethyl α-[3-(2,6-dimethyl-4-pyridyl)anilinomethylene]acetoacetate using 3-(2,6-dimethyl-4-pyridyl)aniline.

EXAMPLE 11 — Ethyl α-[3-(3,5-dimethyl-4-pyridyl)anilinomethylene]acetoacetate using 3-(3,5-dimethyl-4-pyridyl)aniline.

Following the procedure described in Example 2 but using in place of ethyl α-[3-(4-pyridyl)anilinomethylene]acetoacetate a molar equivalent quantity of the appropriate ethyl α-(3-PY-anilinomethylene)acetoacetate, the compounds of Examples 12–18 are obtained:

EXAMPLE 12 — 3-Acetyl-1,4-dihydro-4-oxo-7-(3-pyridyl)quinoline using ethyl α-[3-(3-pyridyl)anilinomethylene]acetoacetate.

EXAMPLE 13 — 3-Acetyl-1,4-dihydro-7-(2-methyl-4-pyridyl)-4-oxoquinoline using ethyl α-[3-(2-methyl-4-pyridyl)anilinomethylene]acetoacetate.

EXAMPLE 14 — 3-Acetyl-1,4-dihydro-7-(3-methyl-4-pyridyl)-4-oxoquinoline using ethyl α-[3-(3-methyl-4-pyridyl)anilinomethylene]acetoacetate.

EXAMPLE 15 — 3-Acetyl-7-(2-ethyl-4-pyridyl)-1,4-dihydro-4-oxoquinoline using ethyl α-[3-(2-ethyl-4-pyridyl)anilinomethylene]acetoacetate.

EXAMPLE 16 — 3-Acetyl-7-(3-ethyl-4-pyridyl)-1,4-dihydro-4-oxoquinoline using ethyl α-[3-(3-ethyl-4-pyridyl)anilinomethylene]acetoacetate.

EXAMPLE 17 — 3-Acetyl-1,4-dihydro-7-(2,6-dimethyl-4-pyridyl)-4-oxoquinoline using ethyl α-[3-(2,6-dimethyl-4-pyridyl)anilinomethylene]acetoacetate.

EXAMPLE 18 — 3-Acetyl-1,4-dihydro-7-(3,5-dimethyl-4-pyridyl)-4-oxoquinoline using ethyl α-[3-(3,5-dimethyl-4-pyridyl)anilinomethylene]acetoacetate.

Following the procedure described in Example 3 but using in place of 3-acetyl-1,4-dihydro-4-oxo-7-(4-pyridyl)-quinoline and ethyl tosylate a molar equivalent quantity each of the respective appropriate 3-acetyl-1,4-dihydro-4-oxo-7-PY-quinoline and/or alkylating agent, the compounds of Examples 19–26 are obtained:

EXAMPLE 19 — 3-Acetyl-1-ethyl-1,4-dihydro-4-oxo-7-(4-pyridyl)quinoline using 3-acetyl-1,4-dihydro-4-oxo-7-(4-pyridyl)quinoline and diethyl sulfate or ethyl iodide. Similarly, using said 7-(4-pyridyl) compound and a molar equivalent quantity of dimethyl sulfate, n-propyl iodiode, isobutyl bromide or n-hexyl chloride in place of ethyl tosylate, there is obtained 3-acetyl-1,4-dihydro-1-methyl-4-oxo-7-(4-pyridyl)-quinoline, 3-acetyl-1,4-dihydro-4-oxo-1-n-propyl-7-(4-pyridyl)quinoline, 3-acetyl-1,4-dihydro-1-isobutyl-4-oxo-7-(4-pyridyl)quinoline or 3-acetyl-1-n-hexyl-1,4-dihydro-4-oxo-7-(4-pyridyl)quinoline, respectively.

EXAMPLE 20 — 3-Acetyl-1-ethyl-1,4-dihydro-4-oxo-7-(3-pyridyl)quinoline using 3-acetyl-1,4-dihydro-4-oxo-7-(3-pyridyl)quinoline.

EXAMPLE 21 — 3-Acetyl-1-ethyl-1,4-dihydro-7-(2-methyl-4-pyridyl)-4-oxoquinoline using 3-acetyl-1,4-dihydro-7-(2-methyl-4-pyridyl)-4-oxoquinoline.

EXAMPLE 22 — 3-Acetyl-1-ethyl-1,4-dihydro-7-(3-methyl-4-pyridyl)quinoline using 3-acetyl-1,4-dihydro-7-(3-methyl-4-pyridyl)-4-oxoquinoline.

EXAMPLE 23 — 3-Acetyl-1-ethyl-7-(2-ethyl-4-pyridyl)-1,4-dihydro-4-oxoquinoline using 3-acetyl-7-(2-ethyl-4-pyridyl)-1,4-dihydro-4-oxoquinoline.

EXAMPLE 24 — 3-Acetyl-1-ethyl-7-(3-ethyl-4-pyridyl)-1,4-dihydro-4-oxoquinoline using 3-acetyl-7-(3-ethyl-4-pyridyl)-1,4-dihydro-4-oxoquinoline.

EXAMPLE 25 — 3-Acetyl-1-ethyl-1,4-dihydro-7-(2,6-dimethyl-4-pyridyl)-4-oxoquinoline using 3-acetyl-1,4-dihydro-7-(2,6-dimethyl-4-pyridyl)-4-oxoquinoline.

EXAMPLE 26 — 3-Acetyl-1-ethyl-1,4-dihydro-7-(3,5-dimethyl-4-pyridyl)-4-oxoquinoline using 3-acetyl-1,4-dihydro-7-(3,5-dimethyl-4-pyridyl)-4-oxoquinoline.

Following the procedure described in Example 4 but using a molar equivalent quantity of the appropriate 3-acetyl-1-alkyl-1,4-dihydro-4-oxo-7-PY-quinoline in place of 3-acetyl-1-ethyl-1,4-dihydro-4-oxo-7-(4-pyridyl)oxoquinoline, there are obtained the corresponding 1-alkyl-1,4-dihydro-4-oxo-7-PY-3-quinolinecarboxylic acids of Examples 27–37.

EXAMPLE 27 — 1,4-Dihydro-1-methyl-4-oxo-7-(4-pyridyl)-3-quinolinecarboxylic acid using 3-acetyl-1,4-dihydro-1-methyl-4-oxo-7-(4-pyridyl)quinoline.

EXAMPLE 28 — 1,4-Dihydro-4-oxo-1-n-propyl-7-(4-pyridyl)-3-quinolinecarboxylic acid using 3-acetyl-1,4-dihydro-4-oxo-1-n-propyl-7-(4-pyridyl)quinoline.

EXAMPLE 29 — 1,4-Dihydro-1-isobutyl-4-oxo-7-(4-pyridyl)-3-quinolinecarboxylic acid using 3-acetyl-1,4-dihydro-1-isobutyl-4-oxo-7-(4-pyridyl)quinoline.

EXAMPLE 30 — 1-n-Hexyl-1,4-dihydro-4-oxo-7-(4-pyridyl)-3-quinolinecarboxylic acid using 3-acetyl-1-n-hexyl-1,4-dihydro-4-oxo-7-(4-pyridyl)quinoline.

EXAMPLE 31 — 1-Ethyl-1,4-dihydro-4-oxo-7-(3-pyridyl)-3-quinolinecarboxylic acid using 3-acetyl-1-ethyl-1,4-dihydro-4-oxo-7-(3-pyridyl)quinoline.

EXAMPLE 32 — 1-Ethyl-1,4-dihydro-7-(2-methyl-4-pyridyl)-4-oxo-3-quinolinecarboxylic acid using 3-acetyl-1-ethyl-1,4-dihydro-7-(2-methyl-4-pyridyl)-4-oxoquinoline.

EXAMPLE 33 — 1-Ethyl-1,4-dihydro-7-(3-methyl-4-pyridyl)-3-quinolinecarboxylic acid using 3-acetyl-1-ethyl-1,4-dihydro-7-(3-methyl-4-pyridyl)quinoline.

EXAMPLE 34 — 1-Ethyl-7-(2-ethyl-4-pyridyl)-1,4-dihydro-4-oxo-3-quinolinecarboxylic acid using 3-acetyl-1-ethyl-7-(2-ethyl-4-pyridyl)-1,4-dihydro-4-oxoquinoline.

EXAMPLE 35 — 1-Ethyl-7-(3-ethyl-4-pyridyl)-1,4-dihydro-4-oxo-3-quinolinecarboxylic acid using 3-acetyl-1-ethyl-7-(3-ethyl-4-pyridyl)-1,4-dihydro-4-oxoquinoline.

EXAMPLE 36 — 1-Ethyl-1,4-dihydro-7-(2,6-dimethyl-4-pyridyl)-4-oxo-3-quinolinecarboxylic acid using 3-acetyl-1-ethyl-1,4-dihydro-7-(2,6-dimethyl-4-pyridyl)-4-oxoquinoline.

EXAMPLE 37 — 1-Ethyl-1,4-dihydro-7-(3,5-dimethyl-4-pyridyl)-4-oxo-3-quinolinecarboxylic acid using 3-acetyl-1-ethyl-1,4-dihydro-7-(3,5-dimethyl-4-pyridyl)-4-oxoquinoline.

We claim:

1. Lower-alkyl α-(3-PY-anilinomethylene)acetoacetate where PY is 4(or 3)-pyridyl or 4(or 3)-pyridyl having one or two non-tertiary lower-alkyl substituents.

2. Ethyl α-(4-pyridyl)anilinomethylene)acetoacetate] according to claim 1.

* * * * *

UNITED STATES PATENT AND TRADEMARK OFFICE
CERTIFICATE OF CORRECTION

PATENT NO. : 4,107,167
DATED : August 15, 1978
INVENTOR(S) : Roman R. Lorenz and William H. Thielking It is certified that error appears in the above-identified patent and that said Letters Patent are hereby corrected as shown below:

Column 1, lines 51-56, structure V,

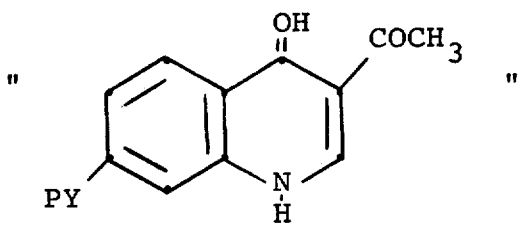

should read

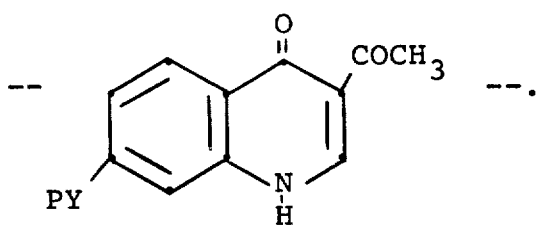

UNITED STATES PATENT AND TRADEMARK OFFICE
CERTIFICATE OF CORRECTION

PATENT NO. : 4,107,167
DATED : August 15, 1978
INVENTOR(S) : Roman R. Lorenz and William H. Thielking It is certified that error appears in the above-identified patent and that said Letters Patent are hereby corrected as shown below:

Column 1, structure VA,

" 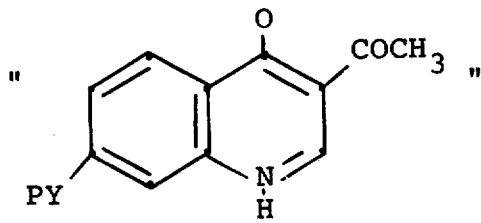 "

should read

-- 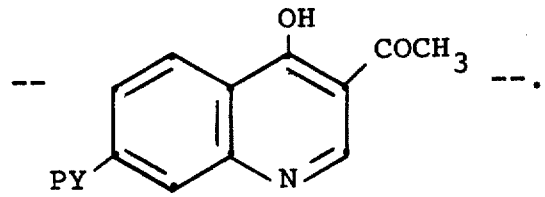 --.

UNITED STATES PATENT AND TRADEMARK OFFICE
CERTIFICATE OF CORRECTION

PATENT NO. : 4,107,167

DATED : August 15, 1978

INVENTOR(S) : Roman R. Lorenz and William H. Thielking

It is certified that error appears in the above-identified patent and that said Letters Patent are hereby corrected as shown below:

Column 4, line 10, "presence of absence" should read -- presence or absence --.

Column 8, line 66, "α-(4-pyridyl)anilinomethylene)-acetoacetate]" should read -- α-[3-(4-pyridyl)anilinomethylene]acetoacetate --.

Signed and Sealed this

Nineteenth Day of August 1980

[SEAL]

Attest:

SIDNEY A. DIAMOND

Attesting Officer

Commissioner of Patents and Trademarks